United States Patent [19]
Sugaya

[11] Patent Number: 5,447,690
[45] Date of Patent: Sep. 5, 1995

[54] CHEMICAL ANALYSIS SYSTEM

[75] Inventor: Fumio Sugaya, Kanagawa, Japan

[73] Assignee: Fuji Photo Film Co., Ltd., Kanagawa, Japan

[21] Appl. No.: 253,607

[22] Filed: Jun. 3, 1994

Related U.S. Application Data

[63] Continuation of Ser. No. 5,442, Jan. 19, 1993, abandoned.

[30] Foreign Application Priority Data

Jan. 16, 1992 [JP] Japan ................................. 4-005508
Jan. 31, 1992 [JP] Japan ................................. 4-016098

[51] Int. Cl.$^6$ .......................................... G01N 35/10
[52] U.S. Cl. ................................. 422/64; 422/63;
422/66; 422/104; 435/312; 435/809; 436/43;
436/46; 436/48; 436/805
[58] Field of Search ........................... 422/63-67,
422/102, 104; 436/43, 46, 47, 48, 905; 435/805,
809, 312

[56] References Cited

U.S. PATENT DOCUMENTS

| | | | |
|---|---|---|---|
| 3,992,158 | 11/1976 | Przybylowicz et al. | |
| 4,142,863 | 3/1979 | Covington | 422/63 |
| 4,151,931 | 5/1979 | Schrer et al. | 221/226 |
| 4,187,077 | 2/1980 | Covington et al. | 422/63 |
| 4,190,420 | 2/1980 | Covington et al. | 422/63 |
| 4,279,861 | 7/1981 | Jessop | 422/67 |
| 4,292,272 | 9/1981 | Kitajima et al. | 422/57 |
| 4,296,069 | 10/1981 | Smith et al. | 422/64 |
| 4,568,519 | 2/1986 | Hamilton et al. | 422/64 |
| 4,855,109 | 8/1989 | Muraishi et al. | 422/63 |
| 5,030,418 | 7/1991 | Miyata | 422/63 |
| 5,034,191 | 7/1991 | Porte | 422/64 |
| 5,049,359 | 9/1991 | Azuma et al. | 422/67 |
| 5,053,198 | 10/1991 | Quenin | 422/64 |
| 5,075,079 | 12/1991 | Kerr et al. | 422/64 |
| 5,154,889 | 10/1992 | Muraishi | 422/65 |
| 5,178,835 | 1/1993 | Uekusa et al. | 422/66 |
| 5,192,506 | 3/1993 | Kureshy et al. | 422/64 |

FOREIGN PATENT DOCUMENTS

| | | |
|---|---|---|
| 0064691 | 4/1982 | European Pat. Off. |
| 0180792 | 10/1985 | European Pat. Off. |
| 0304838 | 8/1988 | European Pat. Off. |
| 0397256 | 5/1990 | European Pat. Off. |
| 0458138 | 5/1991 | European Pat. Off. |
| 0474145 | 3/1992 | European Pat. Off. |
| 53-21677 | 7/1978 | Japan. |
| 55-164356 | 12/1980 | Japan. |
| 9000909 | 2/1990 | WIPO. |

*Primary Examiner*—James C. Housel
*Assistant Examiner*—Long V. Le
*Attorney, Agent, or Firm*—Sughrue, Mion, Zinn, Macpeak & Seas

[57] ABSTRACT

A chemical analysis system has a chemical analysis film cartridge having a box-like casing for accommodating therein a plurality of chemical analysis films which are stacked in a predetermined direction. Each chemical analysis film is composed of a base and a reagent layer formed on the base. A spring is provided on the inner side of a first end wall of the casing and urges the stack of the chemical analysis films toward a second end wall of the casing, the first and second end walls being opposed to each other in the predetermined direction. The casing is provided with a first opening which is formed in a side wall of the casing at a portion near the second end wall to permit only the chemical analysis film adjacent to the second end wall to pass therethrough in the direction perpendicular to the predetermined direction and with a second opening which is formed in the second end wall and through which a suction cup for taking out the chemical analysis film through the first opening gains access to the chemical analysis film adjacent to the second end wall.

6 Claims, 5 Drawing Sheets

CHEMICAL ANALYSIS SYSTEM

This is a continuation of application Ser. No. 08/005,442 filed Jan. 19, 1993.

BACKGROUND OF THE INVENTION

1. Field of the Invention

This invention relates to a chemical analysis system using a chemical analysis film which has a reagent layer whose optical density changes upon reaction with a specific biochemical component contained in a sample liquid such as blood or urine.

2. Description of the Prior Art

Quantitative or qualitative analysis of a specific component in a sample liquid is a common operation carried out in various industrial fields. Especially, quantitative analysis of a chemical component or a solid component contained in body fluid such as blood or urine is very important in the field of clinical biochemistry.

A chemical analysis system using a dry-type chemical analysis slide with which a specific component contained in a sample liquid can be quantified through a droplet of the sample liquid deposited on the slide is shown. See Japanese Patent Publication No. 53(1978)-21677, U.S. Pat. No. 3,992,158, Japanese Unexamined Patent Publication No. 55(1980)-164356, U.S. Pat. No. 4,292,272 for example. When such a dry-type chemical analysis slide is used, the sample liquid can be analyzed more easily and more quickly than when the conventional wet analysis method is used, and accordingly the dry-type chemical analysis slide is very convenient for medical facilities, laboratories and the like where lots of sample liquids have to be analyzed.

When chemical components or the like contained in a sample liquid are analyzed using such a dry-type chemical analysis slide, a droplet of the sample liquid is deposited on the slide and is held at a constant temperature for a predetermined time in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the slide is projected onto the slide and the optical density of the slide is measured. Then the component to be analyzed is quantified on the basis of the optical density using a calibration curve which represents the relation between the concentration of the biochemical component and the optical density.

The chemical analysis slide generally comprises a chemical analysis film composed of a base film of plastic or the like and a reagent layer formed on the base film and a plastic frame which holds the chemical analysis film flat, the chemical analysis film being apt to warp into a roof tile shape when it dries.

Though the reagent in the reagent layer does not react without water, it can begin to react as soon as it absorbs moisture. Accordingly, in order to obtain precise result of analysis, it is most important to keep the reagent layer dry until it is used.

Further, in order to facilitate automation of the analysis, it is preferred that the chemical analysis slides can be smoothly fed one by one.

There has been known a cartridge in which a stack of a plurality of (e.g., fifty) chemical analysis slides is accommodated. (For example, see U.S. Pat. Nos. 4,151,931, 4,187,077, 4,190,420 and 4,279,861.)

In the cartridge, each time the uppermost slide in the stack is pushed laterally out of the cartridge, a lift member is inserted into the cartridge below the lowermost slide and the stack of the slides is lifted upward by the distance corresponding to the thickness of one slide. Such an operation is repeated until all the slides in the cartridge are taken out.

Since a large number of chemical analysis slides are used in a short time, the cartridge must be large in size. Moreover, a plurality, equal to the number of the biochemical components to be analyzed, of the cartridges must be provided in the analysis system, which results in increase in the size of the system.

Further, in such a chemical analysis slide, the frame is so expensive that the cost of biochemical analysis increases.

SUMMARY OF THE INVENTION

In view of the foregoing observations and description, the primary object of the present invention is to provide a chemical analysis system which can use a chemical analysis film cartridge which is small in size and eliminates the need for a frame which keeps the chemical analysis film flat, thereby reducing the cost of the biochemical analysis.

In accordance with the present invention, there is provided a chemical analysis system having a chemical analysis film cartridge containing therein a plurality of substantially rectangular chemical analysis films without a frame each composed of a transparent base and a reagent layer formed thereon, an incubator for incubating the chemical analysis film, and a film transfer means which takes out the chemical analysis film from the cartridge and loads the same in the incubator.

Preferably, said chemical analysis film cartridge comprises a box-like casing for accommodating therein a plurality of said chemical analysis films which are stacked in a predetermined direction and each of which is composed of a base and a reagent layer formed on the base, and an urging means which is provided on the inner side of a first end wall of the casing and urges the stack of the chemical analysis films toward a second end wall of the casing, the first and second end walls being opposed to each other in the predetermined direction, the casing being provided with a first opening which is formed in a side wall of the casing at a portion near the second end wall to permit only the chemical analysis film adjacent to the second end wall to pass therethrough in the direction perpendicular to the predetermined direction and with a second opening which is formed in the second end wall and through which a film takeout means for taking out the chemical analysis film through the first opening gains access to the chemical analysis film adjacent to the second end wall.

Preferably, the incubator comprises a body portion having therein a heating means, a film holding portion for accommodating the chemical analysis film, a light measuring window formed in the bottom of the film holding portion, and a cover provided over the film holding portion to be opened and closed, the film holding portion being in the form of a recess which is formed on the upper surface of the body portion and is provided with corner portions which protrude inward at portions of the film holding portion opposed to the respective corners of the chemical analysis film so that the chemical analysis film cannot contact with the side wall of the film holding portion but at the four corners thereof.

Since the chemical analysis film cartridge used in the chemical analysis system of the present invention contains therein chemical analysis films without frames, it can be smaller in size than the conventional cartridge in which chemical analysis slides each comprising a chemical analysis film and a plastic frame are contained, and accordingly the analysis system can be smaller in size. As the cartridge is generally stored in a dehumidifying container, dehumidifying efficiency can be improved when chemical analysis films without frames are contained in the cartridge.

Further since the chemical analysis film cartridge can supply a chemical analysis film without a frame, the cost of the biochemical analysis can be lowered by an amount corresponding to the frame. Further since the chemical analysis film itself is very small in size and weight, the stack of the chemical analysis films can be lifted toward the second end wall of the casing by an urging means such as a spring provided in the casing, which eliminates the need for an external lifting means and permits simplification of the cartridge and the film lifting mechanism.

Further being small in size and thickness (e.g., 15 mm×15 mm×0.5 mm), the chemical analysis film cannot be smoothly taken out by a protruding member which is used to protrude the chemical analysis slide in the conventional cartridge. In the case of the cartridge used in the system of the present invention, the second opening formed in the second end wall gives the film takeout means, such as a suction cup, access to the chemical analysis film. When a means such as a suction cup which can hold the chemical analysis film is used as the film takeout means, the chemical analysis film can be smoothly taken out without damaging it.

Since the first opening is shaped and sized to permit only one of the films nearest to the second end wall to pass therethrough, the film can be smoothly taken out and at the same time, a large amount of moisture cannot enter the casing.

Use of the chemical analysis film cartridge where chemical analysis films which have no frame and curl in dry state are contained gives rise to the following problems. That is, in the conventional chemical analysis system using a cartridge containing therein chemical analysis films flatten by plastic frames (chemical analysis slides), the incubator has film holding portions in the form of slits open to the side surface of the incubator and the slides are inserted into the slits, for instance, by a reciprocating claw. (See U.S. Pat. Nos. 4,296,069, 4,568,519 and the like.) However it is difficult to insert a chemical analysis film without a frame into the slit since the chemical analysis film without a frame curls in a dry state as described above. Further since the sample liquid deposited on the film at the center thereof spreads circularly and can reach a side of the reagent layer, a part of the sample liquid can overflow and adheres to the side surface of the film without a frame. If the side surface of the film is brought into contact with a side wall of the film holding portion of the incubator, the sample liquid on the side surface of the film will contaminate the side wall of the film holding portion and can transfer to the film which is inserted next and spread to the reagent layer thereof, which can adversely affect the accuracy of the analysis.

In the incubator used in the system of the present invention, the chemical analysis film without frame can be easily loaded in the film holding portion from above since the film holding portion is in the form of a recess open upward, and at the same time, since the recess is arranged so that the film cannot contact with the side wall of the recess but at the four corners thereof, the sample liquid adhering to the side surface of the film cannot contaminate the recess. The incubator can be smaller in size than the conventional incubator in which the chemical analysis slide (the chemical analysis film with a frame) is incubated.

Further, though, in the conventional incubator where the film holding portions are in the form of slits open in the side surface of the body portion, the film holding portions can be arranged in only one row, the film holding portions can be arranged in a plurality of concentric rows and accordingly a larger number of film holding portions can be compactly formed in the incubator of the present invention where the film holding portions are in the form of recesses open upward.

When the incubator is to be provided with a plurality of film holding portions, it is preferred that the film holding portions be arranged in a plurality of concentric rows.

DESCRIPTION OF THE PREFERRED EMBODIMENTS

Figure 1:
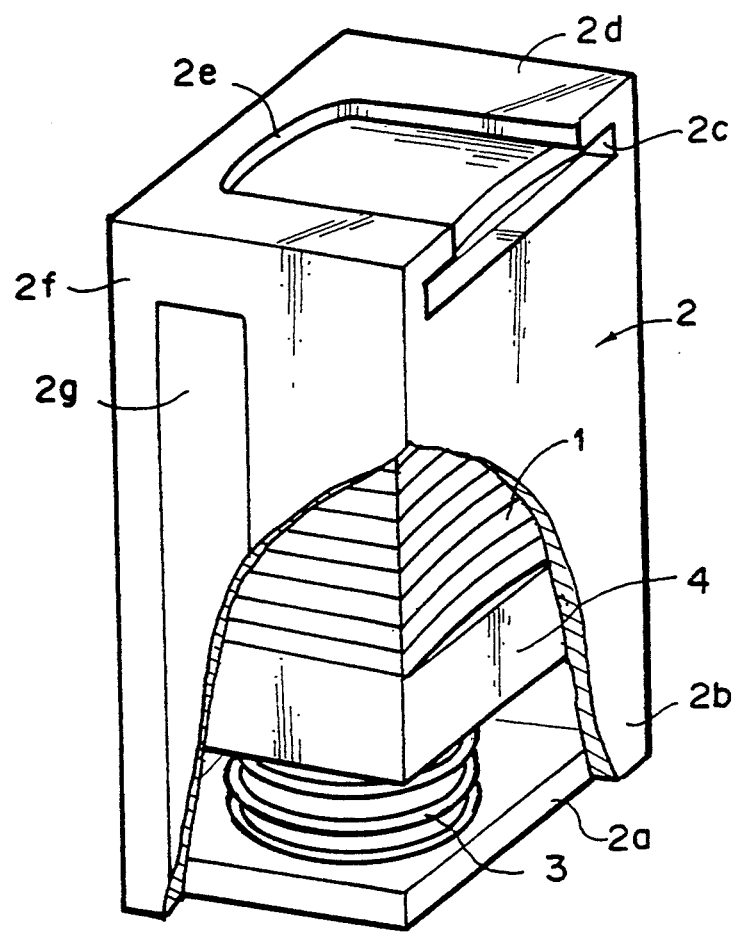
FIG. 1 is a perspective view showing a chemical analysis film cartridge which can used in a chemical analysis system of the present invention.

In FIG. 1, a chemical analysis film cartridge comprises a box-like casing 2 for accommodating a stack of chemical analysis films 1, a spring member 3 mounted on the inner side of the bottom wall 2a of the casing 2, a support member 4 which is mounted on the top of the spring member 3 and on which the stack of the chemical analysis films 1 is placed. A first opening 2c is formed in one side wall 2b of the casing 2 at a portion near to the top wall 2d of the casing 2. The first opening 2c is shaped and sized to permit only the uppermost film of the stack to pass therethrough. A U-shaped second opening 2e, which gives a suction cup (not shown) for holding the chemical analysis film, access to the uppermost film is formed in the top wall 2d of the casing 2.

On the outer surface of a side wall 2f of the casing 2, there are disposed magnetic stripes 2g which have information recorded thereon such as properties of the chemical analysis films 1 accommodated in the cartridge.

Figure 2:
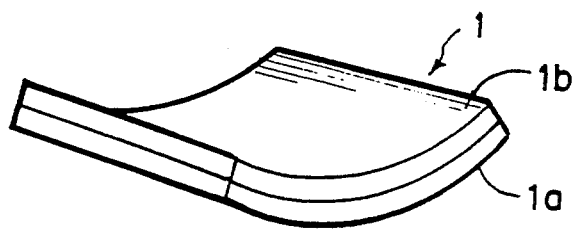
FIG. 2 is a perspective view showing the chemical analysis film to be contained in the cartridge.

The chemical analysis film 1 comprises a base 1a formed of polyethylene terephthalate or the like and a reagent layer 1b, containing therein a developing layer, formed on the base 1a as shown in FIG. 2. In the dry state before use, the chemical analysis film 1 curls toward the reagent layer 1b though it must be substantially flat when it is used.

A plurality of (e.g., 100) chemical analysis films 1 are stacked with the base 1a of each film 1 facing upward and the stack of the films 1 is placed on the support member 4.

The bottom wall 2a of the casing 2 is removable from the side walls of the casing 2 and is inserted into the side walls with the stack of the chemical analysis films 1 placed thereon so that the uppermost film is pressed against the inner side of the top wall 2d. The bottom wall 2a is fixed there by a suitable means (not shown).

The casing 2 is, for instance, 18 mm × 18 mm × 10 mm in size and about 1 mm in thickness. The casing 2 may be formed of, for instance, light-shielding black ABS resin.

Information relating to the chemical analysis films 1 in the cartridge such as information representing the kind of the chemical analysis films 1, the terms of analysis, the number of the films and the like are magnetically recorded on the magnetic stripes 2g, and a magnetic head in the analysis system reads the information for the subsequent biochemical analysis.

Removing the chemical analysis films 1 from the cartridge will be described with reference to FIGS. 3 and 4, hereinbelow.

Figure 3:
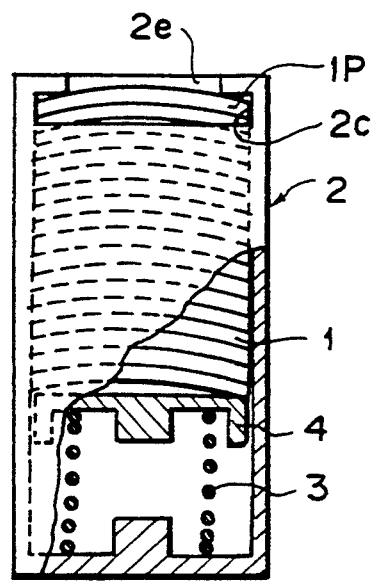
FIG. 3 is a front view partly cut away of the cartridge shown in FIG. 1, FIGS. 4A and 4B are views for illustrating the manner of taking out the film from the cartridge.

As shown in FIG. 3, the chemical analysis films 1 stacked on the support member 4 with the base 1a facing upward to be convex upward are pressed against the inner side of the top wall 2d of the casing 2 under the force of the spring member 3. Even if the curvature of the chemical analysis film 1 varies film to film, there arises no problem so long as they are all positioned to be convex upward. That is, the chemical analysis film 1 never curls toward the base 1a. The force of the spring member 3 is selected so that even if there remains only one chemical analysis film 1 in the cartridge, the spring member 3 can press the film 1 against the inner side of the top wall 2d of the casing 2.

Figure 4A:
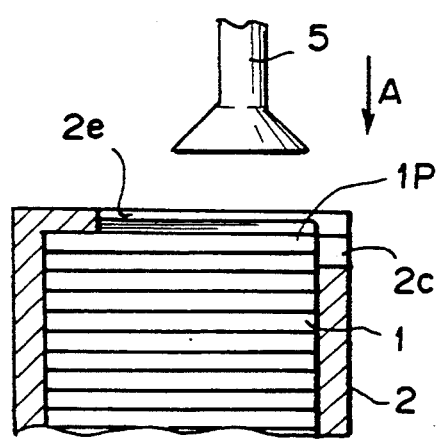
Figure 4B:
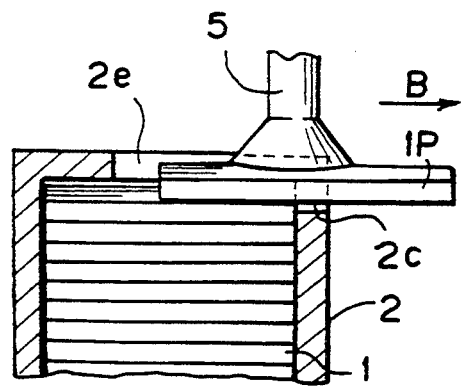

A suction cup 5 is disposed above the second opening 2e of the casing 2, and when the analysis is to be effected, the suction cup 5 is moved downward in the direction shown by the arrow A in FIG. 4A under the control of a controller (not shown) to abut against the uppermost chemical analysis film 1p through the second opening 2e. The suction cup 5 holds the uppermost chemical analysis film 1p under vacuum supplied from a vacuum source (not shown) and then is moved in the direction shown by the arrow B in FIG. 4B through the first opening 2c to transfer the film 1p to a predetermined position in the analysis system. Since the first opening 2c is shaped and sized to permit only the uppermost film of the stack to pass therethrough as described above, the second uppermost film cannot be drawn out together with the uppermost film 1p. Further since the suction cup 5 sucks the base 1a of the film 1, the vacuum force effectively acts on the film 1 and at the same time the suction cup 5 cannot damage the reagent layer 1b.

After the uppermost film 1p is taken out in the manner described above, the stack of the chemical analysis films 1 in the cartridge is lifted upward under the force of the spring member 3 by a distance corresponding to the thickness of one chemical analysis film 1.

In this embodiment, since the stack of the chemical analysis films 1 is resiliently pressed against the inside of the top wall 2d of the casing 2 under the force of the spring member 3, there is no possibility of the film 1 falling out of the cartridge even if the cartridge is vibrated or dropped during storage or transfer.

In contrast with the chemical analysis slide cartridge where a stopper must be provided in order to prevent the slide from falling out of the cartridge, the chemical analysis film cartridge of this embodiment requires no stopper since the chemical analysis film 1 is light in weight and can be firmly held in the cartridge solely by the force of the spring member 3.

The size, color, material and the like may be changed depending on the situation.

Any suitable means may be used in place of the spring member 3 so long as it can surely press the stack of the chemical analysis films 1 against the inside of the top wall 2d of the casing 2.

Though, in the embodiment described above, only one side wall of the casing is provided with the first opening through which the uppermost film is taken out, such an opening may be provided in a plurality of the side walls. In such a case, the second opening through which the suction cup 5 gains access to the uppermost film 1 and slides it through the first opening is shaped to lead to the respective first openings.

Further, though in the embodiment described above, information on the chemical analysis films 1 is recorded on the magnetic stripes, it may be recorded by other recording methods such as that using a bar code.

Figure 5:
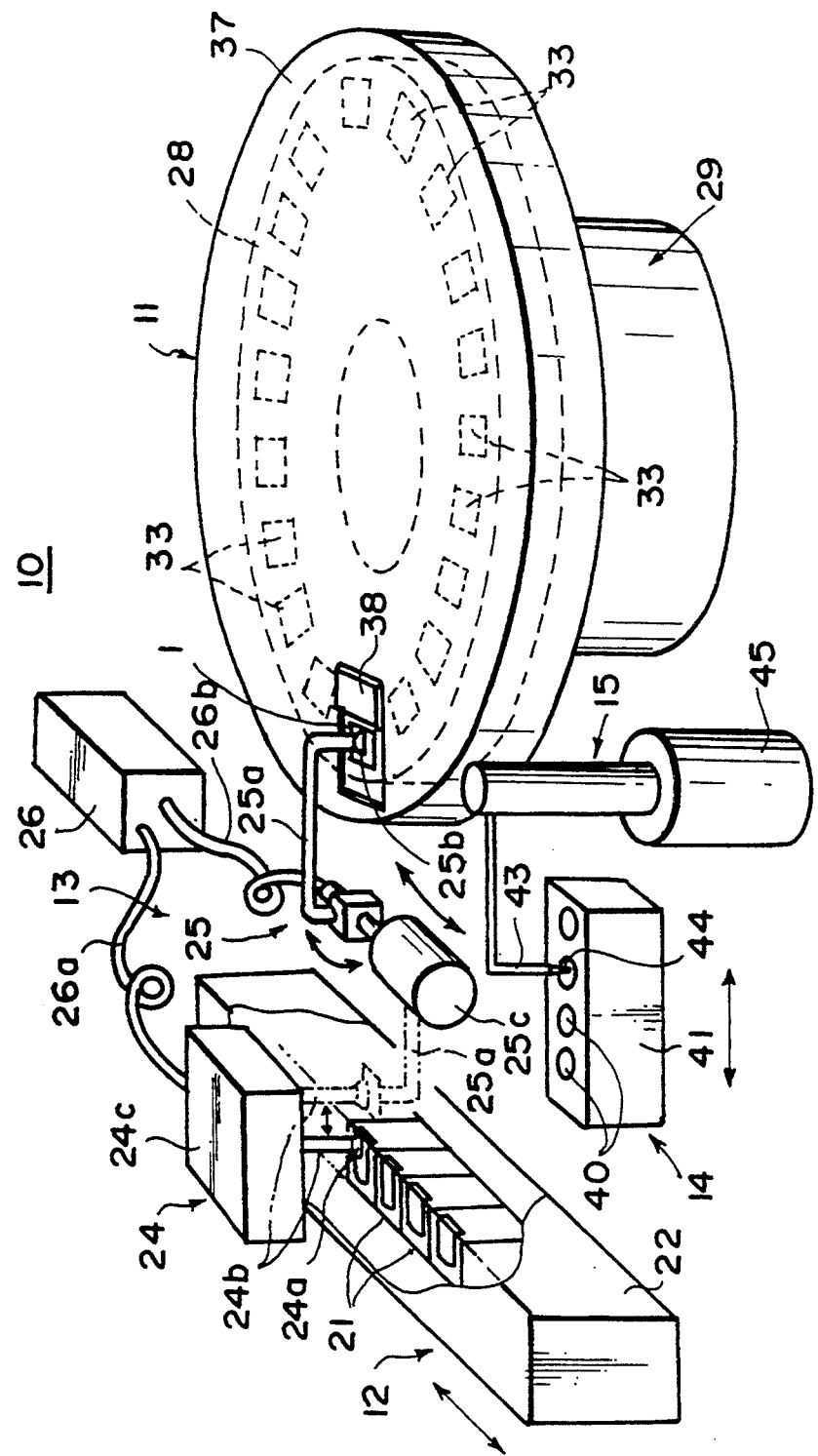
FIG. 5 is a schematic perspective view showing a chemical analysis system in accordance with an embodiment of the present invention.
Figure 6:
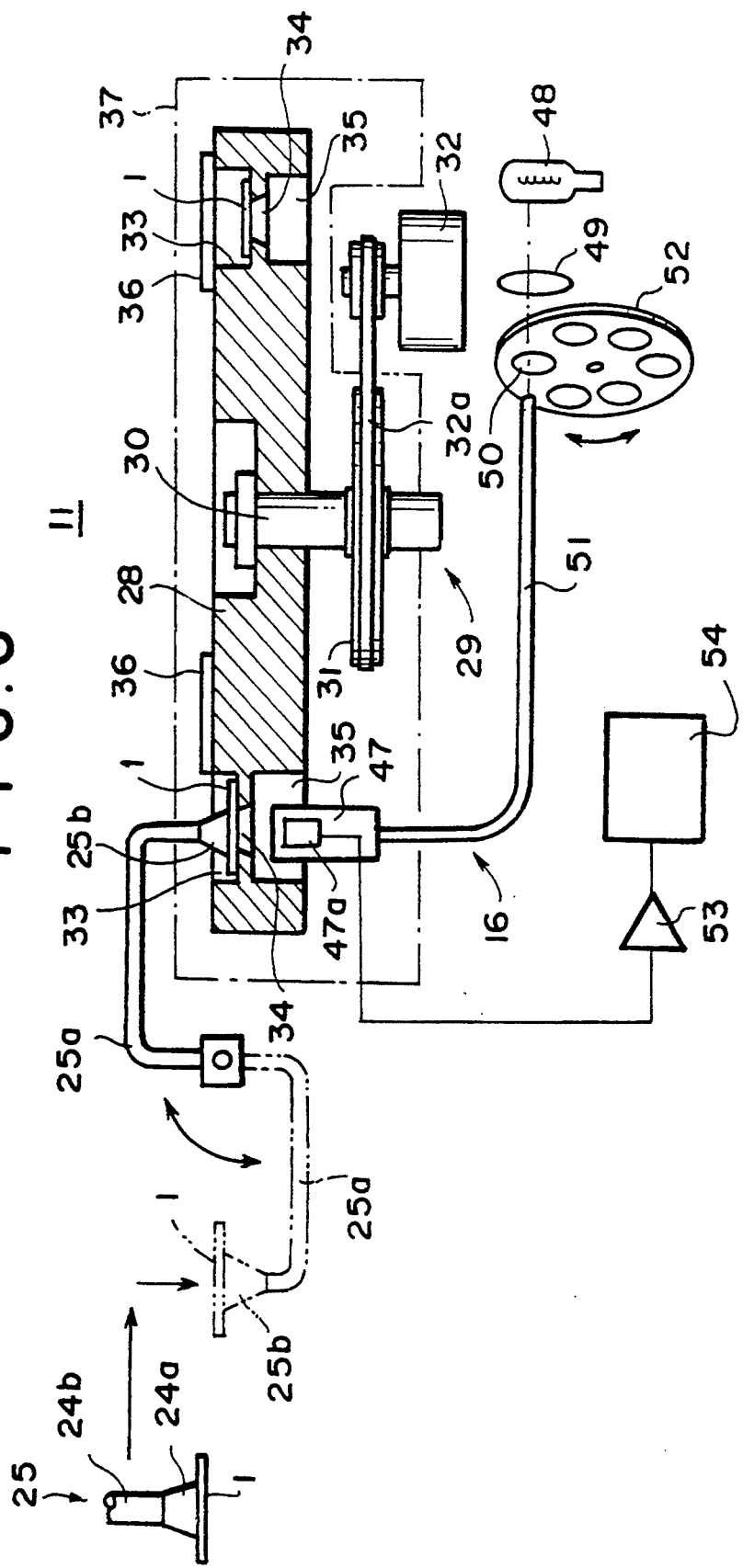
FIG. 6 is a cross-sectional view of the incubator employed in the system.

FIGS. 5 and 6 show a chemical analysis system 10 provided with an incubator which is suitable for incubating chemical analysis films 1 without a frame.

The chemical analysis system 10 comprises an incubator 11 for incubating chemical analysis films 1 (which are rectangular in shape) at a constant temperature for a predetermined time, a film storage means 12 which is disposed on one side of the incubator 11 and in which a plurality of chemical analysis film cartridges 21 are stored, a film transfer means 13 which transfers the chemical analysis films 1 to the incubator 11, a sample liquid supply means 14 which supplies sample liquid, and a depositing means 15 which deposits the sample liquid supplied by the supply means 14 onto the chemical analysis films 1 transferred to the incubator 11.

The chemical analysis film cartridges 21 are of the structure described above in conjunction with FIGS. 1 to 4 and will not be described in detail here.

The film storage means 12 has a cartridge container 22 in which the chemical analysis film cartridges 21 are supported and which is moved back and forth by a driving mechanism (not shown) to bring a selected cartridge to a predetermined position. The cartridge container 22 is provided with a lid member which is opened when the chemical analysis film 1 is taken out of the cartridge 21.

The film transfer means 13 comprises a film takeup mechanism 24 which opens the lid of the cartridge container 22 and takes out the uppermost chemical analysis film 1 in the cartridge 21 in the predetermined position and a film loading mechanism 25 which receives the film 1 from the takeup mechanism 24 and loads it into a film holding portion 33 (to be described later) in the incubator 11 so that the reagent layer 1b faces upward.

The takeup mechanism 24 comprises a suction cup 24a (corresponding to the suction cup 5 described above in conjunction with FIGS. 4A and 4B) mounted on the lower end of a transfer rod 24b which is moved up and down and back and forth by a driving mechanism 24c. The suction cup 24a is provided with vacuum by a suction pump 26 through a vacuum hose 26a. The suction cup 24a is moved downward and then forward to take out the uppermost chemical analysis film 1 from the cartridge 21 in the manner described above. Then the suction cup 24a is lifted and then moved forward to bring the film 1 outside the cartridge container 22.

The loading mechanism 25 comprises a suction cup 25b mounted on a rotary arm 25a which is driven by a motor 25c. The suction cup 25b is provided with vacuum by the suction pump 26 through a vacuum hose 26b. When the suction cup 25b is in the film delivery position shown by the chained line in FIG. 5, the suction cup 25b is directed upward and sucks the film 1 held by the suction cup 24a of the takeup mechanism 24 from below under the force of the vacuum supplied through the vacuum hose 26b. Thus the suction cup 25b sucks the film 1 on the side of reagent layer 1b. When the rotary arm 25a is rotated upward to the film loading position shown by the solid line in FIG. 5, the suction cup 25b is directed downward so that the reagent layer 1b of the film 1 faces upward.

The incubator 11 has a disk-like body portion 28 which is supported for rotation and rotated by a driving mechanism 29. The body portion 28 has a built-in heating means (not shown) and the inner space of the body portion 28 is kept at a predetermined temperature (e.g., 37° C.). As shown in FIG. 6, the driving mechanism 29 comprises a pulley 31 fixed to a rotary shaft 30 mounted on the body portion 28 at the center thereof, a motor 32 and a belt 32a which is passed around the pulley 31 and the output shaft of the motor 32. The driving mechanism 29 intermittently rotates the body portion 28 by a predetermined angle at one time.

A plurality of film holding portions 33 which are in the form of recesses are provided on the upper surface of the body portion 28 at regular intervals in the circumferential direction of the body portion 28. A light measuring window 34 is formed in the bottom of each film holding portion 33 at the center thereof and an annular groove 35 is formed on the lower surface of the body portion 28 to join the light measuring windows 34 of the respective film holding portions 33. A light measuring head 47 (to be described later) is inserted into the annular groove 35. A cover 36 for preventing evaporation of the sample liquid on the film 1 in the film holding portion 33 is provided above each film holding portion 33 to be opened and closed. Though, in this embodiment, the cover 36 is provided one for each film holding portions 33, all the film holding portions 33 may be covered with a single cover.

Figure 7:
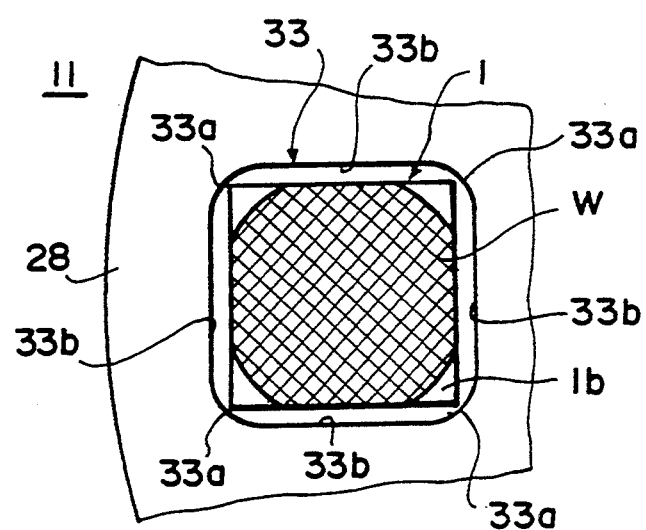
FIG. 7 is a fragmentary plan view of the film holding portion of the incubator.

As shown in FIG. 7, the film holding portion 33 is substantially rectangular in shape which is larger than the chemical analysis film 1. The side wall of the film holding portion 33 protrudes inward at portions corresponding to four corners of the film 1 to form inclined corner portions 33a so that the distance between the opposed sides 33b of the film holding portion 33 reduces toward the side 33b between the opposed sides to smaller than the length of the corresponding side of the film 1, whereby the film 1 accommodated in the film holding portion 33 cannot contact with the side wall 33b of the film holding portion 33 but at the four corners thereof.

An incubator casing 37 covers the upper portion of the incubator 11. The incubator casing 37 is provided with a shutter 38 at a portion opposed to the suction cup 25b of the rotary arm 25a when the rotary arm 25a is in the film loading position. The shutter 38 is normally closed by a suitable urging means (not shown) and is opened by a suitable driving mechanism (not shown) when the rotary arm 25a loads the film 1 to the film holding portion 33 positioned below the shutter 38 and when the depositing means 15 deposits sample liquid on the film 1.

Though not shown, a film discharge means which takes the film 1 out of the incubator 11 after measurement is provided at a portion diametrically opposed to the shutter 38. The film discharge means is similar to the film loading means 25 in structure and a shutter similar to the shutter 38 is provided in the incubator casing 37 at a portion opposed to the film discharge means.

The sample liquid supply means 14 has a sample tray 41 which holds a plurality of sample cups 40 and is moved by a suitable driving mechanism (not shown) to bring the sample cups 40 to a sample takeup position one by one.

The depositing means 15 deposits the sample liquid in the sample cup 40 in the sample takeup position onto the chemical analysis film 1 in the film holding portion 33 below the shutter 38 and has a nozzle 43 which is moved up and down and is rotated by a driving mechanism 45. The nozzle 43 has a pipet-like nozzle tip 44. When the nozzle 43 is moved downward, the nozzle tip 44 is dipped into the sample liquid and sucks the sample liquid in the sample cup 40. Then the nozzle 43 is moved upward and is rotated to the position above the shutter 38, where the nozzle tip 44 discharges the sample liquid therein to deposit it onto the film 1 in the film holding portion 33 below the shutter 38. The nozzle tip 44 is changed when the sample liquid is changed.

The chemical analysis film 1 deposited with the sample liquid is incubated by the incubator 11 and then a measuring means 16 (FIG. 6) measures the optical density of the color formed by coloring reaction between the chemical analysis film 1 and the sample liquid. The measuring means 16 has the aforesaid light measuring head 47 which projects measuring light containing therein a predetermined wavelength onto the reagent layer 1b through the base 1a and detects the reflected light. That is, light emitted from a light source (lamp) 48 enters the light measuring head 47 through a lens 49, a filter 50 and an optical fiber 51 and is caused to impinge upon the reagent layer 1b through a lens in the light measuring head 47. The light reflected from the reagent layer 1b is detected by a photodetector 47a in the light measuring head 47. A plurality of filters 51 having different properties are mounted on a rotary disk 52 and one of the filters 51 is selected by rotating the rotary disk 52 according to the term of analysis.

The light reflected from the reagent layer 1b bearing thereon optical information on the amount of the coloring matter formed in the reagent layer 1b by the coloring reaction impinges upon the photodetector 47a and the intensity of the reflected light is converted into an electric signal, which is input into a determining circuit 54 by way of an amplifier 53. The determining circuit 54 quantifies a predetermined biochemical component in the sample liquid through the optical density of the coloring matter in the reagent layer 1b which is determined on the basis of the level of the electric signal input from the photodetector 47a.

In the chemical analysis system 10, the measurement is effected in the following manner. That is, first the film takeup mechanism 24 takes out a chemical analysis film 1 from one of the cartridge 21 which contains therein chemical analysis films 1 suitable for the analysis to be effected. Then the film takeup mechanism 24 delivers the film 1 to the film loading mechanism 24 and the film loading mechanism 24 inserted the film 1 into film holding portion 33 of the incubator 11 with the reagent layer 1b facing upward. Thereafter, the depositing means 15 dips the nozzle tip 44 into the sample liquid in the sample cup 40 in the sample takeup position and causes it to suck the sample liquid in a predetermined amount. Then the depositing means 15 moves the nozzle tip 44 above the film 1 and then lowers the nozzle tip 44 and causes the nozzle tip 44 to drop a predetermined amount of sample liquid on the reagent layer 1b of the film 1. The sample liquid spreads over the reagent layer 1b and mixed with the reagent.

As described above, the film 1 curls in the dry state as shown in FIG. 2 and uncurls substantially flat in response to deposition of the sample liquid. Coloring reaction is caused when the film 1 with the sample liquid is heated to a predetermined temperature by the incubator 11, and the optical density of the coloring matter is measured by the light measuring head 47 after a predetermined time or at predetermined intervals.

When the sample liquid is deposited on the film 1 at the center thereof, the sample liquid spreads circularly as shown in FIG. 7 (where the sample liquid is indicated at W). When the sample liquid W reaches a side of the reagent layer 1b, a part of the sample liquid W can overflow and adheres to the side surface of the film 1 though does not drop to the bottom of the film holding portion 33. If the film 1 is brought into contact with the side walls 33b, the sample liquid will contaminate the side wall 33b of the film holding portion 33. However, in this embodiment, the film 1 cannot contact with the side walls 33b of the film holding portion 33 but at the four corners thereof by virtue of the corner portions 33a of the film holding portion 33 as described above. The sample liquid cannot reach the four corners of the film 1.

The shape of the corner portion 33a need not be limited to that in the embodiment described above but may be various so long as the side surfaces of the film 1 cannot contact with the side walls 33b of the film holding portion 33.

Though, in the incubator 11 in the embodiment described above, the film holding portions 33a are arranged in a single row on the upper surface of the body portion 28 in the circumferential direction thereof, they may be arranged in a plurality of concentric rows in order to increase the number of the film holding portions 33. In such a case, the film transfer means 13 should be arranged to be able to load the film 1 in the film holding portions 33 in the inner row(s) and the depositing means 15 should be arranged to be able to deposit the sample liquid on the films 1 in the film holding portions 33 in the inner row(s).

In the film storage means 12, the film cartridges 21 may be circularly arranged. Further the nozzle tip 44 may be washed instead of changing it when the sample liquid is changed.

What is claimed is:
1. A chemical analysis system comprising:
  a chemical analysis film cartridge containing therein a plurality of substantially rectangular chemical analysis films without a frame, each composed of a transparent base and a reagent layer formed thereon, an incubator for incubating the chemical analysis film, and a film transfer means for removing the chemical analysis film from the cartridge and loading the chemical analysis film in the incubator,
  said chemical analysis film cartridge comprising a casing for accommodating therein a plurality of said chemical analysis films which are stacked in a predetermined direction and each of which is composed of a base and a reagent layer formed on the base, and an urging means which is provided on an inner side of a first end wall of the casing for urging the stack of the chemical analysis films toward a second end wall of the casing, the first and second end walls being opposed to each other in said predetermined direction, the casing having a first opening which is formed in a side wall of the casing at a portion near the second end wall to permit only the chemical analysis film adjacent to the second end wall to pass therethrough in the direction perpendicular to the predetermined direction and the casing having a second opening which is formed in the second end wall and through which a film takeout means of said film transfer means for taking out the chemical analysis film through the first opening gains access to the chemical analysis film adjacent to the second end wall, and
  said incubator comprising a body portion having therein a heating means, a substantially rectangular film holding portion for accommodating the chemical analysis film, a light measuring window formed in a bottom of the film holding portion, and a cover provided over the film holding portion to be opened and closed, the film holding portion being in the form of a recess which is formed on an upper surface of the body portion and is provided with corner portions which protrude inward at portions of the film holding portion opposed to the respective corners of the chemical analysis film so that the chemical analysis film cannot come into contact with a side wall of the film holding portion but contacts only said corner portions.

2. A chemical analysis system as defined in claim 1 in which the chemical analysis films are stacked in the casing of the cartridge with the reagent layer facing toward said first end wall of the casing.

3. A chemical analysis system as defined in claim 1 or 2 in which information relating to the chemical analysis films contained in the casing is provided on an outer surface of the casing.

4. A chemical analysis system as defined in claim 1 in which a plurality of said film holding portions are formed on the upper surface of the body portion of the incubator.

5. A chemical analysis system as defined in claim 4 in which said film holding portions are arranged in a plurality of concentric rows.

6. A chemical system as defined in claim 1 in which the film takeout means comprises a suction means; and
  said suction means takes out the chemical analysis film adjacent to the second end wall from the chemical analysis film cartridge by gaining access to the chemical analysis film adjacent to the second end wall by passing through the second opening, grasping the chemical analysis film adjacent to the second end wall by applying a vacuum, and moving the chemical analysis film adjacent to the second end wall through the first opening.

* * * * *